United States Patent [19]

Van Heertum et al.

[11] 4,221,799
[45] Sep. 9, 1980

[54] SUBSTITUTED PYRIDINE METHYL ESTERS OF TETRAMETHYL CYCLOPROPANE CARBOXYLIC ACIDS AND THEIR USE AS INSECTICIDES

[75] Inventors: John C. Van Heertum, Concord; Sudarshan K. Malhotra, Walnut Creek, both of Calif.

[73] Assignee: The Dow Chemical, Midland, Mich.

[21] Appl. No.: 62,452

[22] Filed: Jul. 30, 1979

[51] Int. Cl.² .................. A01N 9/22; C07D 213/64
[52] U.S. Cl. ............................ 424/263; 546/300; 546/301; 546/302
[58] Field of Search .............. 546/300, 301, 302; 424/263

[56] References Cited

U.S. PATENT DOCUMENTS

| | | | |
|---|---|---|---|
| 4,083,714 | 4/1978 | Takahashi et al. | 546/300 |
| 4,133,675 | 1/1979 | Schurter et al. | 546/300 |
| 4,134,751 | 1/1979 | Nishiyama et al. | 546/300 |
| 4,163,787 | 8/1979 | Malhotra et al. | 546/301 |

Primary Examiner—Alan L. Rotman
Attorney, Agent, or Firm—S. Preston Jones; Ronald G. Brookens

[57] ABSTRACT

Substituted pyridine methyl esters of tetramethylcyclopropane carboxylic acids and the optical isomers thereof are prepared which correspond to the formula:

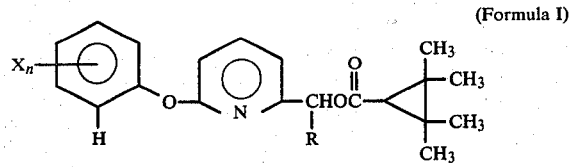

(Formula I)

wherein n represents an integer of 0 to 2; X independently represents alkyl of 1 to 4 carbon atoms, alkoxy of 1 to 4 carbon atoms, alkylthio of 1 to 4 carbon atoms, alkylsulfinyl of 1 to 4 carbon atoms, alkylsulfonyl of 1 to 4 carbon atoms, trifluoromethyl, nitro, cyano, chloro, fluoro, bromo, or 3,4-methylenedioxy (when n is 2 and both X's are taken together); and R represents hydrogen, cyano or ethynyl. These compounds have been found to exhibit a high degree of insecticidal activity and compositions containing said compounds are so employed.

33 Claims, No Drawings

SUBSTITUTED PYRIDINE METHYL ESTERS OF TETRAMETHYL CYCLOPROPANE CARBOXYLIC ACIDS AND THEIR USE AS INSECTICIDES

DESCRIPTION OF PRIOR ART

Various insecticidal compounds which are esters of cyclopropane carboxylic acid are known. 3-(Fluorophenoxy)benzyl substituted cyclopropanecarboxylates are taught in German Pat. No. 2,547,534. 3-Phenoxybenzyl cyclopropane carboxylates are also taught in Japanese Pat. No. 6,011,106. Phenoxy phenyl substituted cyclopropanecarboxylates are taught as insecticides and acaricides in U.S. Pat. No. 3,961,070 and as tick control agents in South African Pat. No. 7,503,211 (based on U.S. patent application Ser. No. 487,417 filed Oct. 7, 1974). Other related substituted phenyl esters of cyclopropane carboxylic acids are taught in French Pat. No. 2,281,918. Various insecticidal 3-(dihalovinyloxy)-benzyl esters of cyclopropane carboxylic acid are taught in German Pat. No. 2,554,883 and ectoparasites are taught to be controlled by the use of 3-phenoxybenzyl esters of spirocarboxylic acids in U.S. Pat. No. 3,962,458. In addition, U.S. Pat. No. 3,979,519 teaches 3-(2,2-dihalovinyloxy)benzyl 2-(2,2-dihalovinyl) 3,3-dialkylcyclopropane carboxylates as insecticides.

SUMMARY OF THE INVENTION

The present invention is directed to substituted pyridine methyl esters of tetramethylcyclopropane carboxylic acids and compositions containing said active compounds and the use of such compositions in the kill and control of various insect pests. The compounds of the present invention correspond to the formula

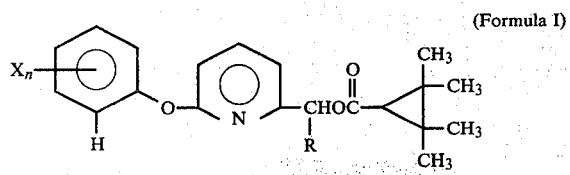

(Formula I)

wherein n represents an integer of 0 to 2; X independently represents alkyl of 1 to 4 carbon atoms, alkoxy of 1 to 4 carbon atoms, alkylthio of 1 to 4 carbon atoms, alkylsulfonyl of 1 to 4 carbon atoms, trifluoromethyl, nitro, chloro, fluoro, bromo or 3,4-methylenedioxy (when n is 2 and both X's are taken together); and R represents hydrogen, cyano or ethynyl.

The compounds of the present invention exist in their optically active isomeric forms, i.e., dextrorotatory and levorotatory forms and the mixtures and racemates thereof are within the scope of the present invention.

In the present specification and claims, the term "alkyl of 1 to 4 carbon atoms" is employed to designate straight chain alkyls of 1 to 4 carbon atoms, branched chain alkyls of 3 or 4 carbon atoms and cyclic alkyls of 3 or 4 carbon atoms such as, for example, methyl, ethyl, propyl, butyl, isopropyl, isobutyl, secondary butyl, tertiary butyl, cyclopropyl and cyclobutyl.

In the present specification and claims, the terms "alkoxy of 1 to 4 carbon atoms", "alkylthio of 1 to 4 carbon atoms", "alkylsulfinyl of 1 to 4 carbon atoms" and "alkylsulfonyl of 1 to 4 carbon atoms" are employed to designate alkoxy and alkylthio groups of the formula —Y—alkyl wherein Y is oxygen, sulfur, sulfinyl or sulfonyl and alkyl is defined as hereinabove set forth for "alkyl of 1 to 4 carbon atoms".

The compounds of the present invention are generally high boiling liquids and are substantially insoluble in water and usually are moderately to highly soluble in common organic solvents.

The compounds of the present invention can be prepared by the reaction of an appropriate substituted phenoxy pyridine methanol or substimethanol and a 2,2,3,3-tetramethylcyclopropane carboxylic acid halide in the presence of a solvent and a hydrogen halide acceptor. The reaction scheme is as follows:

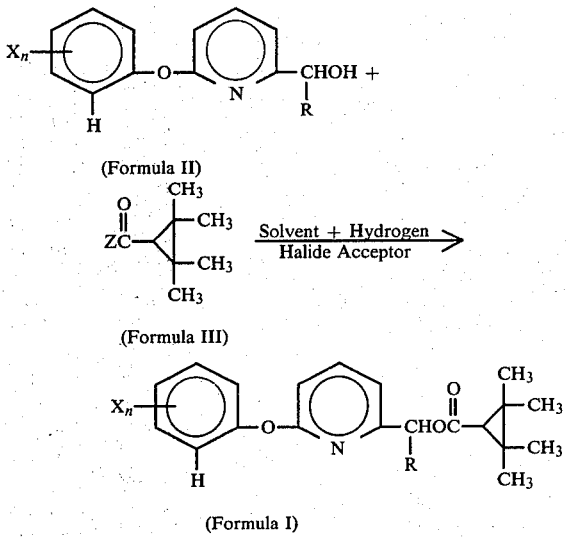

wherein X, n and R are as hereinabove defined and Z is chloro, bromo or fluoro. In carrying out this reaction, the appropriate phenoxy pyridine methanol or substituted methanol and the 2,2,3,3-tetramethylcyclopropane carboxylic acid halide are mixed together with the solvent, conveniently at room temperature. The amounts of the reactants employed are not critical, some of the desired product being obtained when employing the reactants in any amounts. However, the reaction consumes the reactants in amounts representing equimolecular amounts, and the employment of the reactants in such amounts is preferred. The hydrogen halide acceptor is thereafter added to the above mixture, with stirring. The mixture is stirred for from 0.1 to 24 hours and the mixture is then diluted with water and extracted thoroughly with a conventional solvent such as, for example, diethyl ether, hexane, methylene chloride or chloroform. The solvent extract is water washed, dried and concentrated under reduced pressure and if desired, purified by distillation or other conventional methods.

Representative solvents for use in carrying out this reaction include diethyl ether, methylene chloride, glyme and hexane.

Representative hydrogen halide acceptors include conventional bases such as, for example, triethylamine, pyridine, dimethylaniline and the conventional alkali metal bases such as sodium hydroxide, potassium hydroxide, sodium carbonate, potassium bicarbonate, sodium bicarbonate and the like.

DESCRIPTION OF SOME PREFERRED EMBODIMENTS

The following examples illustrate the present invention and the manner by which it can be practiced but, as such, should not be construed as limitations upon the overall scope of the same.

EXAMPLE I:

2,2,3,3-Tetramethylcyclopropane carboxylic acid:cyano(6-phenoxy-2-pyridinyl)methyl ester

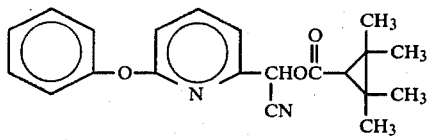

To a cooled solution (10°–15° C.) of 11.7 grams (0.05 mole) of cyano(6-phenoxy-2-pyridine)methanol and 16.5 grams (0.10 mole) of 2,2,3,3-tetramethylcyclopropane carboxylic acid chloride in 100 milliliters of anhydrous ether was slowly added 15 milliliter of triethylamine. The reaction mixture was stirred at room temperature for two (2) hours. The reaction mixture was washed subsequently with water, dilute hydrochloric acid, dilute sodium hydroxide, dilute sodium bisulfite, dilute hydrochloric acid and water and then dried over anhydrous magnesium sulfate and concentrated under vacuo. The residue was dissolved in methylene chloride and filtered. The filtrate was heated at ~40° C. and 5 millimeter of mercury (~40° C./5 mm Hg) for 1 hour. The 2,2,3,3-tetramethylcyclopropane carboxylic acid:-cyano(6-phenoxy-2-pyridinyl)methyl ester product was recovered as a thick oil. The oil had a refractive index of $n_D^{25} = 1.5425$. The structure of the product was confirmed by its nuclear magnetic resonance spectrum (NMR). Upon analysis, the product was found to have carbon, hydrogen and nitrogen contents of 71.24, 6.22 and 8.22 percent, respectively, as compared with the theoretical contents of 71.98, 6.33 and 8.00 percent, respectively, as calculated for the above named compound. (Compound No. 1).

EXAMPLE II:

2,2,3,3-Tetramethylcyclopropane carboxylic acid:(6-phenoxy-2-pyridinyl)methyl ester

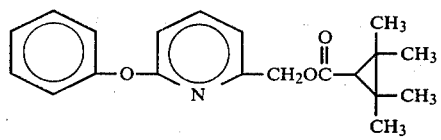

A mixture was prepared by admixing 3.0 grams (0.02 mole) of 6-(phenoxy)picolinalcohol, 2.4 grams (0.01 mole) of 2,2,3,3-tetramethylcyclopropane carboxylic acid chloride, 100 milliliters of methylene chloride and 10 milliliters of triethylamine. The reaction mixture was agitated at room temperature for 24 hours. The mixture was then subsequently washed with dilute hydrochloric acid, dilute sodium hydroxide, dilute sodium bisulfite, dilute hydrochloric acid, water and dried over anhydrous magnisium sulfate. The solvent was removed by evaporation and the mixture heated for 2 hours at 120° C./0.02 mm to remove any low boiling impurities. The 2,2,3,3-tetramethylcyclopropane carboxylic acid:(6-phenoxy-2-pyridinyl)methyl ester was recovered as a dark oil in a yield of 3.0 grams. The product had a refractive index of 1.5440 and the structure of the product was confirmed by NMR. Upon analysis, the product was found to have carbon, hydrogen and nitrogen contents of 73.25, 7.15 and 4.44 percent, respectively, as compared with the theoretical contents of 73.82, 7.12 and 4.30 percent, respectively, as calculated for the above named compound. (Compound No. 2).

EXAMPLE III 2,2,3,3-Tetramethylcyclopropane carboxylic acid:cyano(6-(3-fluorophenoxy)-2-pyridinyl)methyl ester

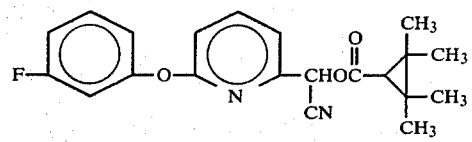

A solution of 4.1 grams (0.017 mole) of cyano(6-(3-fluorophenoxy)-2-pyridine) methanol, 3.0 grams (0.019 mole) of 2,2,3,3-tetramethylcyclopropane carboxylic acid chloride, 75 milliliters of anhydrous ether and 5 milliliters of triethylamine was prepared and stirred at room temperature for ~4 hours. The mixture was filtered through silica gel and the silica gel rinsed with ether. The filtrate was concentrated by evaporating off the solvent. The crude product was then heated at 110° C./0.03 mm Hg to remove low boiling impurities leaving 5.7 grams of crude 2,2,3,3-tetramethylcyclopropane carboxylic acid:cyano(6-(3-fluorophenoxy)-2-pyridinyl)methyl ester. The product was a viscous dark brown oil having a refractive index of $n_D^{25} = 1.5360$. The structure of the product was confirmed by its nuclear magnetic resonance spectrum (NMR). In addition, upon analysis, the product was found to have carbon, hydrogen and nitrogen contents of 67.96, 5.46 and 7.49 percent, respectively, as compared with the theoretical contents of 68.46, 5.75 and 7.60 percent, respectively, as calculated for the above-named compound (Compound No. 3).

EXAMPLE IV:

2,2,3,3-Tetramethylcyclopropane carboxylic acid:cyano(6-(4-methoxyphenoxy)-2-pyridinyl)methyl ester

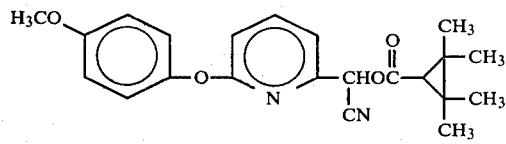

A solution of 3.0 grams (0.012 mole) of cyano(6-(4-methoxyphenoxy)-2-pyridine)methanol and 4.8 grams (0.012 mole) of 2,2,3,3-tetramethylcyclopropane carboxylic acid chloride, 75 milliliters of anhydrous ether and 5 milliliters of triethylamine was prepared. The reaction mixture was stirred at room temperature for 2 hours. The mixture was filtered through silica gel and the silica gel extracted thoroughly with ether. The ether solvent was removed by evaporation under reduced pressure. The crude 2,2,3,3-tetramethylcyclopropane carboxylic acid:cyano(6-(4-methoxyphenoxy)-2-pyridinyl)methyl ester product was heated at 110° C./0.04 mm Hg for 2 hours leaving a viscous brown oil. This oil was recovered in a yield of 6.6 grams and had a refractive index of $n_D{}^{25} = 1.5470$. The structure of the product was confirmed by its nuclear magnetic resonance spectrum (NMR). Upon analysis, the product was found to have carbon, hydrogen and nitrogen contents of 69.32, 6.30 and 7.40 percent, respectively, as compared with the theoretical contents of 69.45, 6.36, and 7.36 percent, respectively, as calculated for the above-named compound (Compound No. 4).

By following the preparative procedures as outlined in the above examples, the following compounds set forth below in Table I are prepared.

Preparation of Starting Materials

The 2,2,3,3-tetramethylcyclopropane carboxylic acid halides employed as starting materials in the preparation of the active compounds of the present invention are well known compounds and are taught in prior art references including A. P. Meshcheryakov et. al., Izvest. Akad. Nauk S.S.S.R., Otdel. Khim. Nauk 1960 (Chem. Abst. 54 24436d (1954)); which teaches the above carboxylic acids as the free acid. These above acids can be converted to the corresponding acid halide by conventional procedures such as, for example, reacting the acid at a temperature of from about room temperature to about 90° C. with a thionyl halide such as thionyl chloride, thionyl bromide or thionyl fluoride or a phosphorus halide such as phosphorus trichloride or phosphorus oxychloride in the presence of an organic

TABLE 1

| Compound Number | $X_n$ | R | Molecular Weight | Refractive Index $n_D{}^{25}$ | Calculated C | Calculated H | Calculated N | Found C | Found H | Found N |
|---|---|---|---|---|---|---|---|---|---|---|
| 5 | 4-Cl; 3-CH₃ | —CN | 398.89 | 1.5696 | 66.24 | 5.81 | 7.02 | 66.03 | 5.36 | 6.34 |
| 6 | 4-Cl; 2-CH₃ | —CN | 398.89 | 1.5466 | 66.24 | 5.81 | 7.02 | 65.63 | 5.74 | 7.05 |
| 7 | 4-Cl | —CN | 384.86 | 1.5533 | 65.53 | 5.50 | 7.28 | 65.35 | 5.52 | 7.18 |
| 8 | 3-CF₃ | —CN | 418.42 | | | | | | | |
| 9 | 3-CF₃ | —H | 393.41 | | | | | | | |
| 10 | 2-CF₃ | —C≡CH | 417.43 | | | | | | | |
| 11 | 4-F | —CN | 368.41 | 1.5319 | 68.46 | 5.75 | 7.60 | 68.32 | 5.67 | 7.53 |
| 12 | 4-CH₃ | —CN | 364.45 | 1.5691 | 72.50 | 6.64 | 7.69 | 72.25 | 6.18 | 7.81 |
| 13 | 3-C₂H₅ | —CN | 378.48 | | | | | | | |
| 14 | 2-C₂H₅ | —C≡CH | 377.49 | | | | | | | |
| 15 | 3-i-C₃H₇ | —H | 367.49 | | | | | | | |
| 16 | 4-Br | —CN | 429.32 | 1.5623 | 58.75 | 4.93 | 6.53 | 58.31 | 4.86 | 6.38 |
| 17 | 2,4-di-Br | —H | 483.21 | | | | | | | |
| 18 | 2,3-di-NO₂ | —H | 415.41 | | | | | | | |
| 19 | 4-OCH₃ | —H | 355.44 | | | | | | | |
| 20 | 2-OCH₃ | —CN | 380.45 | | | | | | | |
| 21 | 3,4-methylenedioxy | —CN | 394.43 | 1.5542 | 66.99 | 5.62 | 7.10 | 66.50 | 5.58 | 6.92 |
| 22 | 2-OC₄H₉ | —C≡CH | 429.56 | | | | | | | |
| 23 | 4-SO₂C₄H₉ | —CN | 470.59 | 1.5444 | 66.64 | 6.71 | 6.22 | 63.39 | 6.60 | 5.83 |
| 24 | 4-OC₄H₉ | —CN | 422.53 | 1.5340 | 71.06 | 7.16 | 6.63 | 71.17 | 7.17 | 6.44 |
| 25 | 3,5-di-CH₃ | —H | 353.47 | | | | | | | |
| 26 | 3,5-di-CH₃ | —CN | 378.48 | | | | | | | |
| 27 | — | —C≡CH | 349.43 | 1.5454 | 75.62 | 6.64 | 4.01 | 75.24 | 6.66 | 3.86 |
| 28 | 2-F | —CN | 368.41 | 1.5523 | 68.46 | 5.75 | 7.60 | 66.93 | 5.28 | 7.38 |
| 29 | 4-SCH₃ | —CN | 396.51 | 1.5664 | 66.64 | 6.10 | 7.07 | 66.39 | 6.12 | 6.63 |
| 30 | 3,4-di-Cl | —CN | 419.31 | 1.5593 | 60.15 | 4.81 | 6.68 | 59.66 | 4.75 | 6.48 |
| 31 | 3,5-di-SCH₃ | —C≡CH | 441.62 | | | | | | | |
| 32 | 3-CH₃; 5-C₄H₉ | —CN | 420.56 | | | | | | | |
| 33 | 3,5-di-OC₄H₉ | —H | 469.63 | | | | | | | |
| 34 | 2-Cl; 4-Br | —CN | 463.77 | | | | | | | |
| 35 | 4-CN | —CN | 375.43 | | | | | | | |
| 36 | 3-t-C₄H₉ | —CN | 406.53 | 1.5278 | 73.86 | 7.44 | 6.89 | 73.30 | 7.71 | 6.41 |
| 37 | 3-Br | —CN | 429.32 | 1.5575 | 59.87 | 4.80 | 6.35 | 59.04 | 5.00 | 6.68 |
| 38 | 2-Cl; 4-CF₃ | —CN | 452.86 | | | | | | | |
| 39 | 4-SC₄H₉ | —CN | 438.59 | 1.5580 | 68.46 | 6.90 | 6.39 | 68.30 | 6.79 | 5.69 |
| 40 | 3-Cl | —CN | 384.86 | 1.5446 | 65.53 | 5.50 | 7.28 | 65.06 | 5.50 | 7.09 |
| 41 | 3,5-di-CF₃ | —CN | 486.42 | | | | | | | |
| 42 | 3,5-di-CF₃ | —H | 461.41 | | | | | | | |
| 43 | 3,5-di-Cl | —CN | 419.31 | 1.5630 | 60.15 | 4.81 | 6.68 | 59.32 | 4.61 | 6.21 |
| 44 | 3,5-di-CN | —CN | 388.43 | | | | | | | |
| 45 | 3-OCH₃; 4-OC₂H₅ | —CN | 424.50 | | | | | | | |
| 46 | 3-OCH₃ | —CN | 380.45 | | | | | | | |
| 47 | 4-SOCH₃ | —CN | 412.50 | 1.5694 | 64.05 | 5.86 | 6.79 | 63.42 | 5.73 | 6.08 |
| 48 | 4-SO₂CH₃ | —CN | 428.51 | 1.5514 | 64.68 | 5.92 | 6.86 | 64.81 | 5.91 | 5.74 |
| 49 | 3-NO₂ | —H | 370.41 | | | | | | | |
| 50 | 4-NO₂ | —CN | 395.42 | | | | | | | |
| 51 | 4-Cl | —H | 359.84 | 37°–38° C.[a] | 66.75 | 6.16 | 3.89 | 66.64 | 6.19 | 3.91 |

[a] compound was white solid, melting point given above solvent such as benzene, hexane or a benzene-hexane mixture.

The phenoxypyridine methanol or substituted methanol used as starting materials and corresponding to the formula

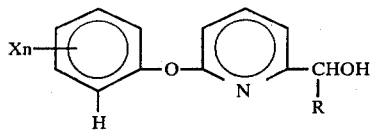

(Formula II)

wherein X, n and R are as hereinbefore defined, can be prepared by a variety of procedures depending upon the R substituent.

For those compounds of Formula II wherein R is hydrogen, the compounds can be prepared by the reaction of an appropriate phenoxypyridine carboxylic acid methyl ester of the formula

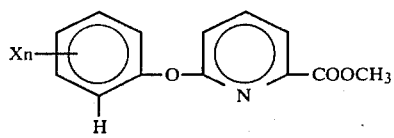

(Formula IV)

wherein X and n are as hereinbefore defined with sodium borohydride in the presence of a solvent.

In carrying out this reaction, the ester reactant is dissolved in a solvent such as methanol, or ethanol and the mixture cooled to a temperature of from about 0° to about 15° C. The sodium borohydride is thereafter added thereto while the temperature is maintained in the above range. The mixture is maintained under these conditions until gas evolution is complete. Thereafter, the solvent is removed by evaporation and the residue taken up in a solvent such as, for example, diethyl ether. This mixture is water washed, washed with dilute hydrochloric acid (5–10%), dried and the solvent removed by evaporation to give the alcohol product. If desired, the product can be further purified.

EXAMPLE V 6-(Phenoxy)picolinalcohol

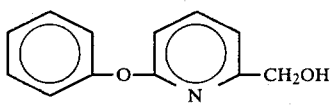

A solution was prepared by dissolving 5.1 grams (0.022 mole) of 6-(phenoxy)methyl picolinate in ~250 milliliters of methanol. The solution was cooled to 10° C. and 7.6 grams (0.2 mole) of sodium borohydride was added thereto portionwise over 1 hour while the temperature was maintained at ~30° C. Foaming occurred during the addition, and when it ceased, the methanol was removed by evaporation. The residue which remained was dissolved in ether, and the resulting solution water washed, washed with dilute hydrochloric acid, dried and the solvent removed by evaporation. The tan oil which remained was distilled to give 1.6 grams of 6-(phenoxy)picolinalcohol as an off-white oil. The structure of the product was confirmed by NMR.

By following the preparative procedures as outlined in the above examples, the following compounds are prepared.

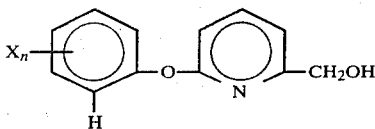

wherein $X_n$ is as follows:

2—$CH_3$; 3—$CH_3$; 4—$CH_3$; 2—$C_2H_5$; 3—$C_2H_5$; 4—$C_2H_5$; 3—i—$C_3H_7$; 3—$C_4H_9$; 4—$C_4H_9$; 4—t—$C_4H_9$; 2—Cl; 3—Cl; 4—Cl; 4—Cl,3—$CH_3$; 4—Cl,2—$CH_3$; 3—$CH_3$,5—$C_4H_9$; 4—F; 4—Br; 2—$CF_3$; 3—$CF_3$; 4—$CF_3$; 2,4-di—Br; 2—Cl,4—Br; 2—Cl,4—$CF_3$; 3,5-di—$CF_3$; 2—$OCH_3$; 3—$OCH_3$; 4—$OCH_3$; 3—$OCH_3$,4—$OC_2H_5$; 2—$OC_4H_9$; 4—$OC_4H_9$; 3,5—$OC_4H_9$; 4—$SCH_3$; 3,5-di—$SCH_3$; 3,5-di—$SOCH_3$; 4—$SC_3H_9$; 4—$SO_2C_4H_9$; 4—CN; 3,5-di—CN; 3—$NO_2$; 4—$NO_2$; 2,3-di—$NO_2$ and 3,4-methylenedioxy.

The phenoxypyridine carboxylic acid methyl esters of the formula

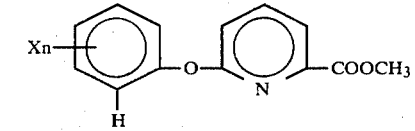

(Formula IV)

wherein X and n are as hereinbefore defined and employed as starting materials can be prepared by reacting an appropriate substituted phenol with a slight excess of the methyl ester of 6-chloropicolinic acid in the presence of a base such as an alkali metal hydride or lower alkoxide such as, for example, sodium, potassium, lithium or cesium hydride or sodium, potassium, lithium or cesium lower alkoxide of 1 to 4 carbon atoms (such as, methoxide, ethoxide, n-propoxide, i-propoxide, n-butoxide, sec-butoxide or t-butoxide), and a solvent such as, for example, diglyme, dimethylsulfoxide or dimethylformamide.

This reaction can be characterized as follows:

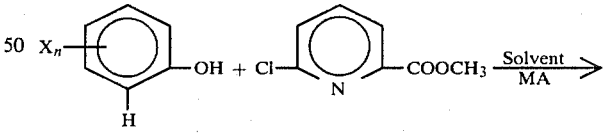

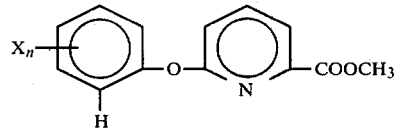

wherein X and n are as hereinbefore defined in MA is an alkali metal hydride or alkoxide.

In carrying out this reaction, the phenol is dissolved in the solvent and the base is slowly added to a solution of the methyl ester dissolved in a solvent at a temperature of from about 100° to about 120° C. After the addition is complete, the temperature is slowly raised to about 130° to about 150° C. The reaction is usually complete in from about 1.5 to about 5.5 hours depending upon the reactants. After the reaction is complete, the reaction mixture is cooled below 70° C. and poured over ice. The product comes down as a solid and is separated by filtration or as an oil and separated by decantation. The crude product is taken up in diethyl ether, washed with water and a base such as, for example, sodium bicarbonate and dried. The solvent is thereafter removed and if desired, the product can be further purified by recrystallization from a solvent such as hexane, benzene, pentane, xylene or by distillation.

EXAMPLE VI 6-(3-Fluorophenoxy)methyl picolinate

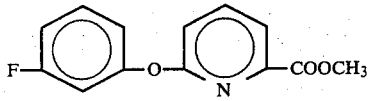

To a solution of 37.7 grams (0.22 mole) of 6-(chloro)-methyl picolinate in 300 milliliters of diglyme was added dropwise a solution comprising 27.2 grams (0.24 mole) of 3-fluorophenol, 27.2 grams (0.24 mole) of potassium t-butoxide in 100 milliliters of diglyme. The addition was carried out at between 120°–130° C. The temperature was slowly raised to 145° C. and after a 2.5 hour reaction time, the reaction was complete. The reaction mixture was cooled to ~70° C. and poured over ice. The solid 6-(3-fluorophenoxy)methyl picolinate which formed was filtered off and dissolved in ether. This solution was washed with water, dilute sodium hydroxide and dried over anhydrous magnesium sulfate and the ether evaporated off. The product which remained as a residue was crystallized from hexane and recovered in a yield of 25.4 grams melting at 54°–55° C. The structure of the compound was confirmed by NMR. Upon analysis, the compound was found to have carbon, hydrogen and nitrogen contents of 62.86, 4.28 and 5.53 percent, respectively, as compared with the theoretical contents of 63.15, 4.08 and 5.67 percent, respectively, calculated for the above-named compound.

By following the preparative procedures as outlined above, employing the appropriate reactants, the following compounds are prepared.

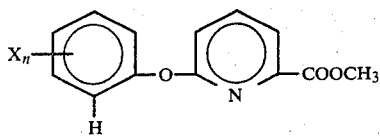

wherein $X_n$ is as follows:

2—CH₃; 3—CH₃; 4—CH₃; 2—C₂H₅; 3—C₂H₅; 4—C₂H₅; 3-i—C₃H₇; 3—C₄H₉; 4—C₄H₉; 4-t—C₄H₉; 2—Cl; 3—Cl; 4—Cl; 4—Cl,3—CH₃; 4—Cl,2—CH₃; 3—CH₃,5—C₄H₉; 4—F; 4—Br; 2—CF₃; 3—CF₃; 4—CF₃; 2,4-di—Br; 2—Cl,4—Br; 2—Cl,4—CF₃; 3,5-di—CF₃; 2—OCH₃; 3—OCH₃; 4—OCH₃; 3—OCH₃,4—OC₂H₅; 2—OC₄H₉; 4—OC₄H₉; 3,5-di—OC₄H₉; 4—SCH₃; 3,5-di—SCH₃; 3,5-di—SOCH₃; 4—SC₄H₉; 4—SO₂C₄H₉; 4—CN; 3,5-di—CN; 3—NO₂; 4—NO₂; 2,3-di—NO₂ and 3,4-methylenedioxy.

For those compounds of Formula II wherein R is —C≡CH, the compounds can be prepared by reacting an appropriate 6-(phenoxy)picolinaldehyde with lithium acetylide. The reaction can be characterized as follows:

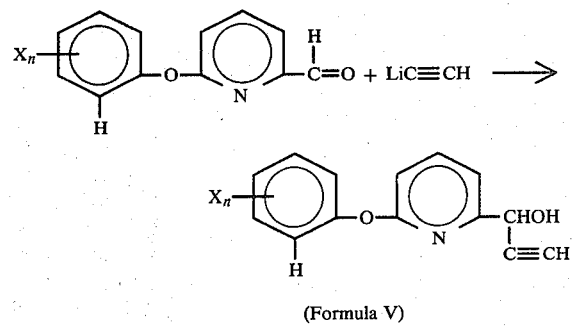

(Formula V)

wherein n and X are as hereinbefore defined.

By following the preparative procedure outlined above, the following compounds can be prepared.

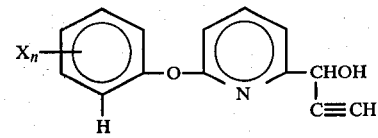

wherein $X_n$ is as follows:

2—CH₃; 3—CH₃; 4—CH₃; 2—C₂H₅; 3—C₂H₅; 4—C₂H₅; 3-i—C₃H₇; 3—C₄H₉; 4—C₄H₉; 4-t—C₄H₉; 2—Cl; 3—Cl; 4—Cl; 4—Cl,3—CH₃; 4—Cl,2—CH₃; 3—CH₃,5—C₄H₉; 4—F; 4—Br; 2—CF₃; 3—CF₃; 4—CF₃; 2,4-di—Br; 2—Cl,4—Br; 2—Cl,4—CF₃; 3,5-di—CF₃; 2—OCH₃; 3—OCH₃; 4—OCH₃; 3—OCH₃,4—OC₂H₅; 2—OC₄H₉; 4—OC₄H₉; 3,5-di—OC₄H₉; 4—SCH₃; 3,5-di—SCH₃; 3,5-di—SOCH₃; 4—SC₄H₉; 4—SO₂C₄H₉; 4—CN; 3,5-di—CN; 3—NO₂; 4—NO₂; 2,3-di—NO₂ and 3,4-methylenedioxy.

For those compounds of Formula II wherein R is —CN, the compounds can be prepared by the reaction, at room temperature of an appropriate 6-(phenoxy)-picolinaldehyde of the formula

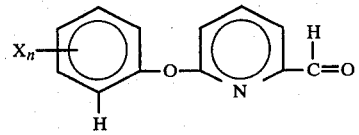

(Formula VI)

wherein X and n are as hereinbefore defined with an excess of an alkali metal cyanide in the presence of an alkali metal bisulfite and water.

In carrying out this reaction, a solution of the aldehyde reactant, the bisulfite and water is reacted with a solution of the cyanide in water. The by-products precipitate out and are separated from the mixture. The aqueous mixture which remains is solvent extracted with a solvent such as benzene, pentane, ether, methylene chloride, hexane, or xylene, water washed and dried and the solvent removed by evaporation leaving the desired product.

EXAMPLE VII

Cyano(6-(3-fluorophenoxy)-2-pyridine)-methanol also known as 6-(3-fluorophenoxy)α-hydroxy-2-pyridine acetonitrile)

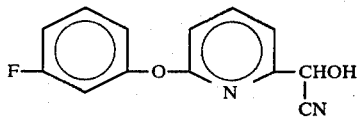

A solution was prepared by mixing 10.6 grams (0.0488 mole) of 6-(3-fluorophenoxy)picolinaldehyde and 5.6 grams (0.0537 mole) of sodium bisulfite in 50 milliliters of water until a solution formed. To this solution was added 2.6 grams (0.0537 mole) of sodium cyanide in 50 milliliters of water. A solid quickly formed and the aqueous mixture which remained was extracted with ether. The ether extract was washed with a 10% sodium bisulfite solution followed by a water wash and dried over magnesium sulfate. The ether was thereafter removed by evaporation. The reaction product was crystallized from hexane to give 12.5 grams of the desired cyano(6-(3-fluorophenoxy)-2-pyridine)methanol product which melted at 73°-74° C. Upon analysis, the product was found to have carbon, hydrogen and nitrogen contents of 63.90, 3.85 and 11.32 percent, respectively, as compared with the theoretical contents of 63.93, 3.71 and 11.47 percent, respectively, calculated for the above-named compound.

By following the preparative procedures as outlined in the above example, the following compounds are prepared.

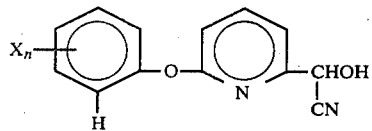

wherein $X_n$ is as follows:
2—CH$_3$; 3—CH$_3$; 4—CH$_3$; 2—C$_2$H$_5$; 3—C$_2$H$_5$; 4—C$_2$H$_5$; 3—i—C$_3$H$_7$; 3—C$_4$H$_9$; 4—C$_4$H$_9$; 4—t—C$_4$H$_9$; 2—Cl; 3—Cl; 4—Cl; 4—Cl,3—CH$_3$; 4—Cl,2—CH$_3$; 3—CH$_3$,5—C$_4$H$_9$; 4—F; 4—Br; 2—CF$_3$; 3—CF$_3$; 4—CF$_3$; 2,4—di—Br; 2—Cl,4—Br; 2—Cl,4—CF$_3$; 3,5—di—CF$_3$; 2—OCH$_3$; 3—OCH$_3$; 4—OCH$_3$; 3—OCH$_3$,4—OC$_2$H$_5$; 2—OC$_4$H$_9$; 4—OC$_4$H$_9$; 3,5—di—OC$_4$H$_9$; 4—SCH$_3$; 3,5—di—SCH$_3$; 3,5—di—SOCH$_3$; 4—SC$_4$H$_9$; 4—SO$_2$C$_4$H$_9$; 4—CN; 3,5—di—CN; 3—NO$_2$; 4—NO$_2$; 2,3—di—NO$_2$ and 3,4-methylenedioxy.

The 6-(phenoxy)picolinaldehydes of the formula (Formula VI)

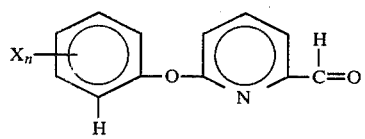

wherein X is alkyl, alkylthio, alkylsulfonyl, trifluoromethyl, 3,4-methylenedioxy, chloro, fluoro or bromo and n is as hereinbefore defined which are employed as starting materials, can be prepared by reacting an appropriate phenoxypyridine carboxylic acid methyl ester with an excess of diisobutyl aluminum hydride in the presence of a solvent such as, toluene, hexane or xylene. This reaction can be characterized as follows:

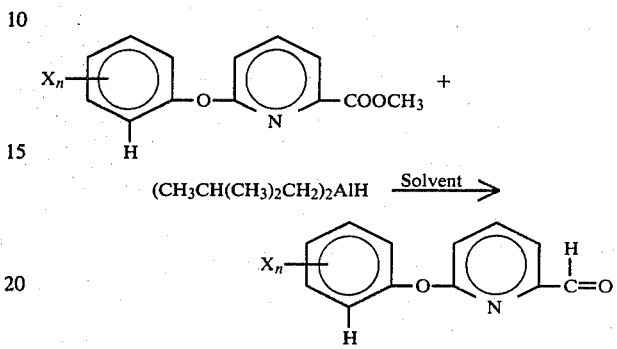

wherein X and n and Y are as hereinabove defined.

In carrying out this reaction, the ester reactant is mixed with the solvent under an inert atmosphere and the mixture cooled to below −50° C. The hydride is slowly added thereto at a temperature below −50° C. Upon completion of the reaction, an acetic acid-water-diethyl ether solution is mixed with the reaction mixture at about −50° C. and the mixture heated slowly to room temperature. The insolubles are removed by filtration and washed with a solvent such as diethyl ether. The filtrate is then followed by a water wash and a wash with sodium bicarbonate and dried. The solvent is removed by evaporation and if desired, the product is further purified by recrystallization from pentane, heptane or benzene and dried.

EXAMPLE VIII 6-(3-Fluorophenoxy)picolinaldehyde

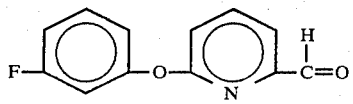

To a stirring mixture of 21.9 grams (0.0849 mole) of 6-(3-fluorophenoxy)methyl picolinate in 150 milliliters of toluene at −50° C. and under a nitrogen atmosphere was slowly added 130 milliliters (0.0121 mole) of diisobutylaluminum hydride (20 percent in hexane) at −50° C. Upon completion of the reaction (as noted by gas-liquid chromatography), 150 milliliters of a solution made from 50 milliliters of acetic acid, 12 milliliters of water and 150 milliliters of ether was slowly added to the reaction mixture at −50° C. The resulting solution was warmed slowly to room temperature. The mixture was thereafter filtered and the filter cake washed thoroughly with ether and the ether solution mixed with the filtrate. The filtrate mixture was washed with water, a sodium bicarbonate solution, dried over anhydrous magnesium sulfate and the ether was removed by evaporation. The 6-(3-fluorophenoxy)-picolinaldehyde product remained as a residue and was purified by crystallization from hexane. The product was recovered in a yield of 13.9 grams and melted at 42°-43° C. The structure was confirmed by NMR. Upon analysis, the product was found to have carbon, hydrogen and nitrogen contents of 66.32, 3.92 and 6.21 percent, respectively, as compared with the theoretical contents of 66.36, 3.71 and 6.45 percent, respectively, as calculated for the above-named compound.

By following the preparative procedures as outlined above, employing the appropriate picolinate reactant, the following compounds are prepared.

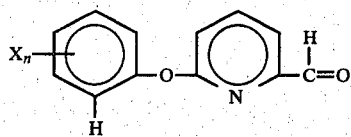

wherein $X_n$ is as follows:

2—$CH_3$; 3—$CH_3$; 4—$CH_3$; 2—$C_2H_5$; 3—$C_2H_5$; 4—$C_2H_5$; 3-i-$C_3H_7$; 3—$C_4H_9$; 4—$C_4H_9$; 4-t—$C_4H_9$; 2—Cl; 3—Cl; 4—Cl; 4—Cl,3—$CH_3$; 4—Cl,2—$CH_3$; 3-$CH_3$,5—$C_4H_9$; 4—F; 4-Br; 2—$CF_3$; 3—$CF_3$; 4—$CF_3$; 2,4-di—Br; 2—Cl,4—Br; 2-Cl,4-$CF_3$; 3,5-di—$CF_3$; 2—$OCH_3$; 3—$OCH_3$; 4—$OCH_3$; 3—$OCH_3$,4—$OC_2H_5$; 2—$OC_4H_9$; 4—$OC_4H_9$; 3,5-di—$OC_4H_9$; 4—$SCH_3$; 3,5-di—$SCH_3$; 3,5-di-$SOCH_3$; 4—$SC_4H_9$; 4—$SO_2C_4H_9$; 4—CN; 3,5-di—CN; 3—$NO_2$; 4—$NO_2$; 2,3-di—$NO_2$ and 3,4-methylenedioxy.

The 6-(phenoxy)picolinaldehydes of the formula

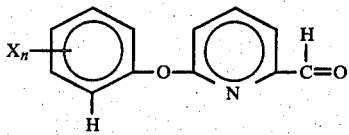

wherein X is cyano or nitro and n is 1 or 2 can be prepared by reacting 6-chloro-picolinaldehyde with the alkali metal salt, for example, sodium, lithium or potassium salt of the appropriately substituted phenol in a solvent such as, for example, monoglyme, diglyme, dimethylformamide or a mixture of any of the above solvents with toluene at a temperature in the range of 25°–150° C. for from ~1 to ~24 hours. At the completion of this reaction, the insolubles are removed by filtration and washed with a solvent such as diethyl ether. The filtrate is then followed by a water wash and a wash with sodium bicarbonate and dried. The solvent is removed by evaporation and if desired, the product is further purified by recrystallization from hexane, pentane, heptane or benzene and dried.

This reaction can be characterized as follows:

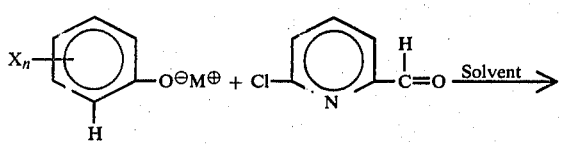

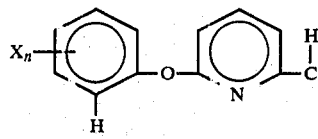

wherein X and n are as hereinabove defined and M is sodium, lithium or potassium.

By following the preparative procedures as outlined above, employing the appropriate substituted phenol and 6-chloro-picolinaldehyde, the following compounds are prepared:

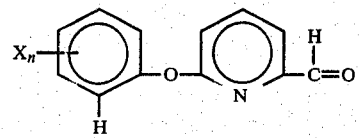

wherein $X_n$ is as follows:

2—CN, 3—CN, 4—CN, 3,4-di—CN, 3,5-di—CN, 2,3-di—CN, 2—$NO_2$, 3—$NO_2$, 4—$NO_2$, 2,3-di—$NO_2$, 3,4-di—$NO_2$ and 3,5-di-$NO_2$.

In accordance with the present invention, it has been discovered that the substituted pyridine methyl esters of tetramethyl cyclopropane carboxylic acid possess insecticidal properties. The compounds have quick knockdown activity and low persistence, as toxic residues.

Because of the "quick knockdown", the subject compounds are particularly suitable for the control, inside houses, barns, warehouses, public buildings, and the like, of pests, including cockroaches, such as the German cockroach, American cockroach, and brown-banded cockroach; beetles, such as the black-carpet beetle, confused flour beetle, saw-tooth grain beetle, and larder beetle; spiders, silverfish, bedbugs; fleas, such as those on bedding used by household pets, and flea larvae; mosquitos; boxelder bugs; spiders; mites; ants; centipedes; and flies, such as hornfly, stable fly and facefly and the common housefly. The subject compounds are highly effective for such indoor control of insect pests and thus are particularly adapted for such employment. In addition, the subject compounds are also useful for the control of lice and ticks and other insects parasitic to animals.

The new compounds of the present invention are very effective for the control of the many insect pests found on the roots or aerial portions of growing plants, including aphids, scale, mites, white files and chewing and sucking insects, such as leafhopper, Southern army worm, two-spotted spider mite, cotton aphid, cabbage looper, western spotted cucumber beetle, bollworm, codling moth, beet armyworm, and tobacco budworm.

The subject compounds, when applied to plants, plant parts, and their habitats to protect the plants from the attack of insect pests, exhibit residual control of the insects over only a relatively short period of time thereby not having appreciable build-up in the environment.

In some procedures, the compounds can be vaporized or sprayed or distributed as aerosols into the air, or onto surfaces in contact with the air. In such applications, the compounds manifest the useful properties hereinbefore described.

The methods of the present invention comprise contacting an insect with an insecticidally effective or inactivating amount of one of the compounds of the present invention.

The contacting can be effected by application of the compound of the habitat of the insects. Representative habitats include soil, air, water, food, vegetation, inert objects stored matter such as grains, other animal organisms, and the like. The inactivation can be lethal, immediately, or with delay, or can be a sub-lethal one in which the inactivated insect is not able to carry out one or more of its normal life processes. This latter situation prevails when one of the systems of the insect, typically the nervous system, is seriously disturbed. A preferred embodiment of the present invention comprises the employment of the present method for the kill and control of insects; such employment gives excellent results, particularly in control of insects that have developed resistance against other pest-control substances.

The inactivation of an insect by the application of an insecticidally effective or inactivating amount of one of the presently claimed compounds is critical to the method of the present invention. The compound can sometimes be employed in unmodified form. Frequently, however, for easier application, the compound is modified by the employment with it of a pesticidal adjuvant or inert carrier therefor. Thus, for example, the present compounds are of very low solubility in water but are relatively soluble in oils, including plant essential oils. Therefore, the practical enjoyment of the beneficial utilities of the present compounds often requires that the compound be admixed with one or more pesticidal adjuvant substances, and the resulting compositions are included within the present invention.

The compositions can be formulated in various forms, such as emulsifiable concentrates, wettable powders, flowable suspension dusts, granules, microencapsulated granules, fine granules, oil sprays, aerosols, heating fumigants (e.g. mosquito coils, electric mosquito killer mat, etc.), fogging mists, non-heating fumigants and poisonous baits and the adjuvant employed can be any one or a plurality of materials including aromatic solvents, petroleum distillates, water, or other liquid carriers, propellant substances, surface-active dispersing agents, light absorbers, and finely divided carrier solids. In such compositions, the adjuvant cooperates with the compound so as to obtain a composition to facilitate the method of the present invention, and to obtain an improved result. The use of either a surface-active dispersing agent or a finely divided carrier solid and the use of both a surface-active dispersing agent and a finely divided carrier solid, simultaneously, constitute preferred embodiments of the method of the present invention. Another preferred embodiment of the present invention is a composition comprising one or more of the presently claimed compounds, an organic liquid as a solvent and carrier therefor, and a propellant material. Numerous other embodiments will become apparent to those skilled in the art in view of the teachings set forth hereinbelow.

The exact concentration of the active compounds in a composition thereof with an adjuvant therefor can vary; it is only necessary that the active compounds be present in a sufficient amount so as to make possible the application of an insecticidally effective or inactivating dosage. Generally, for practical applications, the active compounds can be broadly applied to insect pest organisms or their habitat in compositions containing from about 0.00001 percent to about 98 percent by weight of the active compound.

In the preparation of dust compositions, the product can be compounded with any of the finely divided carrier solids such as pyrophyllite, diatomaceous earth, gypsum and the like. In such operations, the finely divided carrier is ground or mixed with one or more of the active compounds, as active agent, or wetted with a solution of the active agent in a volatile organic solvent. Similarly, dust compositions containing the active product can be similarly compounded from various of the solid dispersing agents, such as fuller's earth, attapulgite and other clays. These dust compositions can be employed as treating compositions or can be employed as concentrates and subsequently diluted with additional solid dispersing agent or with pyrophyllite, diatomaceous earth, gypsum and the like to obtain the desired amount of active agent in a treating composition. Also, such dust compositions can be dispersed in water, with or without the aid of surfactant, to form spray mixtures.

Further, one of the compounds or a dust concentrate composition containing such compound can be incorporated in intimate mixture with surface active dispersing agents such as ionic and nonionic emulsifying agents to form spray concentrates. Such concentrates are readily dispersible in liquid carriers to form sprays containing the toxicant in any desired amount. The choice of dispersing agent and amount thereof employed are determined by the ability of the agent to facilitate the dispersion of the concentrate in the liquid carrier to produce the desired spray composition.

In the preparation of liquid compositions, the compounds of the present invention can be compounded with a suitable water-immiscible organic liquid and surface-active dispersing agent to produce an emulsifiable liquid concentrate which can be further diluted with water and oil to form spray mixtures in the form of oil-in-water emulsions. In such compositions, the carrier comprises an aqueous emulsion, that is, a mixture of water-immiscible solvent, emulsifying agent and water. Preferred dispersing agents to be employed in these compositions are oil-soluble and include the nonionic emulsifiers such as the polyoxyethylene derivatives of sorbitan esters, complex ether alcohols and the like. However, oil-soluble ionic emulsifying agents such as mahogany soaps can also be used. Suitable organic liquids to be employed in the compositions include petroleum oils and distillates, toluene, liquid halohydrocarbons and synthetic organic oils.

When operating in accordance with the present invention, the compound or a composition containing the compound is applied to the insects to be controlled directly, or by means of application to a portion or portions of their habitat in any convenient manner, for example, by means of hand dusters or sprayers or by simple mixing with the food to be ingested by the organisms. Application of the foliage of plants is conveniently carried out with power dusters, boom sprayers and fog sprayers. In such foliar applications, the employed compositions should not contain any appreciable amounts of any phytotoxic diluents. In large scale operations, dusts, or low-volume sprays can be applied from an airplane. The present invention also comprehends the employment of compositions comprising one of the compounds, an adjuvant, and one or more other biologically active materials, such as insecticides, fungicides, miticides, bactericides, nematocides, and the like.

A preferred and especially convenient matter for the application of one or more of the present products comprises the use of a self-pressurized pack formulation which can be used, for example, as a space or surface spray. Such a formulation can comprise one or more of the compounds, an organic liquid as a solvent and vehicle therefor, and a propellant material which can be condensed and compressed gas or a substance which, at room temperature, is a gas under atmospheric pressure but which liquifies under super-atmospheric pressure.

Where the propellant material is of the latter type, the self-pressurized pack formulation is often spoken of as an aerosol. Representative propellants include propane, butane and nitrogen. Generally, the propellant constitutes from 25 to 95 percent by weight of the total self-pressurized pack. As vehicle, there can be employed any liquid in which the desired amount of product is capable of being dispersed; preferred vehicles include petroleum distillates, kerosene, and methylene chloride. The self-pressurized pack formulation can also include other materials, such as other biologically active agents or synergists. For further discussion of the use of self-pressurized pack formulation, see U.S. Pat. Nos. 1,892,750 and 2,321,023.

The compositions of the present invention will be illustrated in further detail below with reference to the examples, but the kinds and mixing proportions of compounds and additives are not limited to those shown in the examples but are variable within wide ranges. In the examples set forth hereinafter, the compounds employed are referred to by the compound number as hereinabove set forth. All parts are based on weight percent of the total composition.

EXAMPLE IX

A series of dust compositions is prepared by individually admixing and pulverizing 3 parts of each of the compounds numbered 2, 3, 4, 8, 9, 13, 14, 15, 17, 20, 23, 25, 27, 31, 38, 42 or 50 with 97 parts of Barden clay to obtain a composition containing 3 percent of the active ingredient. In application, the composition is dusted as such.

EXAMPLE X

Fifty parts of each of the compounds numbered 36, 38, 43, 44, 45, 46, 49 or 51 is individually mixed with 5 parts of a wetting agent (alkylbenzenesulfonate type) and 45 parts of diatomaceous earth and the mixture thoroughly pulverized and blended together to obtain a wettable powder containing 50 percent of active ingredient. In application, the powder is diluted with water and used as a spray.

EXAMPLE XI

A mixture of 5 parts of each of the compounds numbered 2, 5, 7, 13, 20, 23, 27, 30, 31, 35, 47 or 50 with 93.5 parts of clay and 1.5 parts of polyvinyl alcohol is thoroughly kneaded with water and the mixture granulated and dried. The granule composition contains 5 percent of the active ingredient and can be applied as such.

EXAMPLE XII

Twenty-five parts of compounds numbered 48, 50 parts of toluene and 25 parts of Atlox 3404F ® (proprietary material of Imperial Chemical Industries, U.S. which is a polyoxyethylene alkyl aryl ether-alkyl aryl sulfonate blend) are mixed together to obtain an emulsifiable concentrate having an active ingredient concentration of 25 percent. In application, the concentrate is diluted with water and sprayed.

EXAMPLE XIII 7.6 Parts of each of the compounds numbered 7, 8, 9, 13, 15, 19, 20, 21, 30, 31, 32 or 38 with 80.4 parts of purified material of Imperial Chemical Industries, U.S. (which is a polyoxyethylene sorbitol ester) are mixed together to obtain an emulsifiable concentrate having an active ingredient concentration of 7.6%. In application, the preparation is diluted with water and used as a spray.

EXAMPLE XIV

One part of each of the compounds numbered 8, 11, 16, 37, 42 or 44 is mixed with 99 parts of purified kerosene to obtain an oil preparation having an active ingredient concentration of 1 percent. In application, the composition can be atomized or sprayed as is.

The control of pest organisms by the contacting thereof with one or more of the compounds of the present invention is illustrated by the following examples.

EXAMPLE XV

Cylindrical cages about $3\frac{5}{8}$ inches in diameter by $3\frac{1}{4}$ inches high were fitted with wire screens on the top and bottom. Into each cage was placed a predetermined number of German cockroaches. A series of aqueous dispersions, prepared by admixing each of the hereinafter set forth compounds, in various concentrations, with a predetermined amount of water and a surfactant, were sprayed on respective groups of cockroaches through the screen from a distance of about 15 inches. At the same time additional cockroaches were sprayed with a water-surfactant mixture containing no active toxicant to serve as controls. After spraying, the cockroaches were fed a sugar-water diet for 3 days. At the end of this period, the cages were examined to determine the minimum concentration in parts of active compound per million parts of the ultimate composition (PPM) necessary to give at least a 100 percent ($LD_{100}$) kill and control of the cockroaches. The results of this examination are set forth below in Table 2.

TABLE 2

| Compound Number of Active Compound | Minimum Concentration of Active Compound in PPM to give $LD_{100}$ for German Cockroaches |
|---|---|
| 1 | 100 |
| 3 | <25 |
| 4 | >400 |
| 7 | <25 |
| 11 | <25 |
| 12 | 100 |
| 16 | <25 |
| 28 | >400 |
| 43 | 25 |
| Control | — |

EXAMPLE XVI

In each test, an aqueous dispersion was prepared by dispersing a predetermined amount of one of the test compounds and a predetermined amount of a surfactant in a predetermined amount of water. At the same time, a water/surfactant mixture containing none of the compounds was also prepared to serve as a control. Sheets containing egg masses of codling moths are pinned to apples and the egg sheets and apples are drenched with an aqueous dispersion of one of the hereinafter set forth compounds. Separate egg masses on apples were also treated with the control mixture. The egg masses/apples were incubated under conditions conducive to the hatching of the eggs and the growth of the larvae therefrom. Ten days after treatment, the apples were examined for the presence of larvae. Counts of the number of larvae penetration in the treated fruit were compared to the number present in the control to determine the present control obtained with the test compounds.

This examination determined the minimum concentration in parts of the active compound per million parts of the ultimate dispersion necessary to give at least a 70 percent kill and control of codling moth larvae and the results of this examination are set forth below in Table 3.

TABLE 3

| Number of active Compound | Minimum Concentration in PPM of active compound in aqueous dispersion to give $LD_{70}$ for codling moth larvae |
|---|---|
| 1 | <25 |
| 2 | 25 |
| 3 | <25 ($LD_{60}$) |
| 4 | <25 |
| 5 | 100 |
| 6 | 400 |
| 7 | 25 ($LD_{60}$) |
| 11 | <($LD_{60}$) |
| 12 | <25 |
| 16 | <25 ($LD_{60}$) |
| 21 | <100 |
| 27 | 100 |
| 28 | <25 |
| 29 | 100 |
| 37 | <25 |
| 40 | 400 |
| 43 | 400 ($LD_{60}$) |
| Control | — |

EXAMPLE XVII

In each test, seventy-five grams of air-dried soil was placed in an 8-ounce container. To the soil was added sufficient volume of a 400 ppm aqueous dispersion, prepared by admixing a predetermined amount of one of the hereinafter set forth compounds with a predetermined amount of water and a predetermined amount of surfactant, to give various predetermined concentrations of the toxicant in the soil on a soil-chemical basis. The treated soil was air-dried and thoroughly mixed by agitation. To each treated container, and control containers treated with water and surfactant alone, was added 0.5 milliliters of an aqueous suspension of the eggs of the Western spotted cucumber beetle (WSCB) (70–80 eggs of 3–4 days old). Treated soil was used to cover the eggs and corn seed was placed on the soil and covered with additional treated soil. The containers were thereafter maintained under conditions conducive to the growth of the seeds and the hatching of the eggs. Twelve (12) days after treatment, the containers and the plants therein were examined to determine the minimum concentration in parts of active compound per million parts of soil necessary to give at least a 100 percent kill and control of the larvae from the hatched eggs. The results of this examination are set forth below in Table 4.

TABLE 4

| Number of active Compound | Minimun Concentration in PPM of active compound in soi 169 to give a $LD_{100}$ of WSCB larvae |
|---|---|
| 1 | 6.2 |
| 3 | 6.2 |
| 4 | <25 |
| 7 | 25 |
| 11 | 6.2 |
| 12 | <25 |
| 1. | 6.2 |

TABLE 4-continued

| Number of active Compound | Minimun Concentration in PPM of active compound in soi 169 to give a $LD_{100}$ of WSCB larvae |
|---|---|
| 21 | 25 |
| 24 | 25 |
| 28 | 6.2 |
| 37 | 25 |
| 40 | 25 |
| Control | — |

EXAMPLE XVIII

In this operation, aqueous dispersions were prepared by admixing one of the hereinafter set forth compounds with a predetermined quantity of water and a predetermined amount of a surfactant to give aqueous dispersions containing varying predetermined amounts of one of the compounds as the sole active toxicant. Separate cotton plant leaves were thoroughly wetted briefly with one of the dispersions and the wetted leaves placed in an open petri dish and permitted to dry. After the leaves were dry, 5 live beet armyworm larvae were placed in each Petri dish. In identical operations, 5 live beet armyworm larvae were placed in control Petri dishes, the leaf therein have been wetted with a solution containing only water and surfactant. The dishes were maintained under moist conditions conducive for the growth of the beet armyworm larvae for a period of about 5 days. At the end of the 5-day period, the dishes were examined to determine the minimum concentration in parts of the active compound per million parts of the ultimate dispersion necessary to give at least a 100 percent kill and control of the beet armyworm larvae. The results of this examination are set forth below in Table 5.

TABLE 5

| Number of active Compound | Minimum Concentration in PPM of active compound in dispersion to give $LD_{100}$ for beet armyworm larvae |
|---|---|
| 1 | 100 |
| 2 | 400 |
| 3 | 100 |
| 4 | 100 |
| 5 | 100 |
| 6 | 100 |
| 7 | <25 |
| 11 | 100 |
| 12 | <25 |
| 16 | <25 |
| 21 | 400 |
| 27 | <100 |
| 28 | >400 |
| 29 | 400 |
| 30 | 400 |
| 37 | 400 |
| 40 | 400 |
| 43 | 400 ($LD_{40}$) |
| Control | — |

EXAMPLE XIX

In this operation, aqueous dispersions were prepared by admixing one of the hereinafter set forth compounds with a predetermined quantity of water and a predetermined amount of a surfactant to give aqueous dispersions of varying predetermined amounts of one of the compounds as the sole active toxicant. Separate 3 inch discs cut from tobacco plant leaves were thoroughly wetted briefly with one of the dispersions and the wetted leaves placed in an open Petri dish and permitted to dry. After the leaves were dry, 5 live tobacco budworm larvae were placed in each Petri dish. In identical operations, 5 live tobacco budworm larvae were placed in control Petri dishes, the leaf therein having been wetted with a solution containing only water and surfactant. The dishes were maintained under moist conditions conducive for the growth of the tobacco budworm larvae for a period of about 2 days. At the end of the 2-day period, the dishes were examined to determine the minimum concentration in parts of the active compound per million parts of the ultimate dispersion necessary to give at least a 100 percent kill and control of the tobacco budworm larvae. The results of this examination are set forth below in Table 6.

TABLE 6

| Number of active Compound | Minimum Concentration in PPM of active compound in dispersion to give $LD_{100}$ for tobacco budworm larvae |
|---|---|
| 1 | 100 |
| 2 | 400 |
| 3 | 100 |
| 4 | 100 |
| 5 | 400 |
| 7 | <25 |
| 11 | 100 |
| 12 | 400 |
| 16 | <25 |
| 21 | 400 |
| 28 | >400 |
| 29 | 400 ($LD_{80}$) |
| 30 | 100 |
| 40 | 100 ($LD_{80}$) |
| 47 | 400 ($LD_{40}$) |
| Control | — |

EXAMPLE XX

Aqueous dispersions were prepared by admixing one of the hereinafter set forth compounds with a predetermined quantity of water and a predetermined amount of a surfactant to give aqueous dispersions containing varying predetermined amounts of one of the compounds as the sole toxicant. Separate rice plants were dipped into one of the dispersions and permitted to dry. A plastic cylinder was placed around the plants and 10 adult Aster leafhoppers were placed in the cylinder and the cylinder capped. In a like manner, 10 adult Aster leafhoppers were placed on control plants which had been dipped in a solution containing only water and surfactant. The plants were maintained under conditions conducive to the growth of the plants and leafhoppers. After a period of two days, the cylinder and plants were examined to determine the minimum concentration in parts of the active compound per million parts of the ultimate dispersion necessary to give at least 95 percent kill and control of the Aster leafhopper. The results of this examination are set forth below in Table 7.

TABLE 7

| Number of active Compound | Minimum Concentration in PPM of active compound in dispersion to give $LD_{95}$ for Aster leafhoppers |
|---|---|
| 21 | 25 |
| 23 | 400 |
| 24 | 400 |
| 27 | 400 |
| 29 | <100 |
| 37 | <100 |
| 39 | 400 |
| 40 | 400 |
| Control | — |

What is claimed is:

1. A compound corresponding to the formula

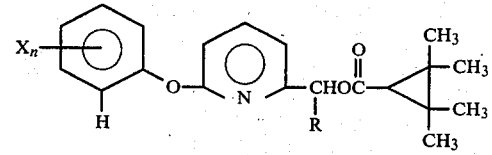

wherein n represents an integer of 0 to 2; X independently represents alkyl of 1 to 4 carbon atoms, alkoxy of 1 to 4 carbon atoms, alkylthio of 1 to 4 carbon atoms, alkylsulfinyl of 1 to 4 carbon atoms, alkylsulfonyl of 1 to 4 carbon atoms, trifluoromethyl, chloro, fluoro, bromo; n represents an integer of 0 to 2; and R represent hydrogen, cyano or ethynyl.

2. A compound as defined in claim 1 wherein R is hydrogen.

3. A compound as defined in claim 1 wherein R is ethynyl.

4. A compound as defined in claim 1 wherein R is cyano.

5. The compound as defined in claim 2 which is 2,2,3,3-tetramethylcyclopropane carboxylic acid:(6-phenoxy-2-pyridinyl)methyl ester.

6. The compound as defined in claim 3 which is 2,2,3,3-tetramethylcyclopropane carboxylic acid:1-(6-phenoxy-2-pyridinyl)-2-propynyl ester.

7. The compound as defined in claim 4 which is 2,2,3,3-tetramethylcyclopropane carboxylic acid:-cyano(6-phenoxy-2-pyridinyl)methyl ester.

8. The compound as defined in claim 4 which is 2,2,3,3-tetramethylcyclopropane caboxylic acid:-cyano(6-(4-methoxyphenoxy)-2-pyridinyl)methyl ester.

9. The compound as defined in claim 4 which is 2,2,3,3-tetramethylcyclopropane carboxylic acid:-cyano(6-(4-chlorophenoxy)-2-pyridinyl)methyl ester.

10. The compound as defined in claim 4 which is 2,2,3,3-tetramethylcyclopropane carboxylic acid:-cyano(6-(3-fluorophenoxy)-2-pyridinyl)methyl ester.

11. The compound as defined in claim 4 which is 2,2,3,3-tetramethylcyclopropane carboxylic acid:-cyano(6-(4-fluorophenoxy)-2-pyridinyl)methyl ester.

12. An insecticidal composition comprising an inert carrier and as the active ingredient, an insecticidally effective amount of a compound corresponding to the formula

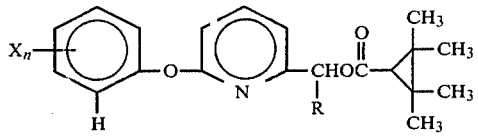

wherein n represents an integer of 0 to 2; X independently represents alkyl of 1 to 4 carbon atoms, alkoxy of 1 to 4 carbon atoms, alkylthio of 1 to 4 carbon atoms, alkylsulfinyl of 1 to 4 carbon atoms, alkylsulfonyl of 1 to 4 carbon atoms, trifluoromethyl, chloro, fluoro, bromo; n represents an integer of 0 to 2; and R represents hydrogen, cyano or ethynyl.

13. A composition as defined in claim 12 wherein R is hydrogen.

14. A composition as defined in claim 12 wherein R is ethynyl.

15. A composition as defined in claim 12 wherein R is cyano.

16. The composition as defined in claim 13 wherein the compound is 2,2,3,3-tetramethylcyclopropane carboxylic acid:(6-phenoxy-2-pyridinyl)-methyl ester.

17. The compound as defined in claim 14 wherein the compound is 2,2,3,3-tetramethylcyclopropane caboxylic acid:(6-phenoxy-2-pyridinyl)-2-propynyl ester.

18. The composition as defined in claim 15 wherein the compound is 2,2,3,3-tetramethylcyclopropane carboxylic acid:cyano(6-phenoxy-2-pyridinyl)-methyl ester.

19. The composition as defined as in claim 15 wherein the compound is 2,2,3,3-tetramethylcyclopropane carboxylic acid:cyano(6-(4-methoxyphenoxy)-2-pyridinyl)methyl ester.

20. The composition as defined in claim 15 wherein the compound is 2,2,3,3-tetramethylcyclopropane carboxylic acid:cyano(6-(4-chlorophenoxy)-2-pyridinyl)methyl ester.

21. The composition as defined in claim 15 wherein the compound is 2,2,3,3-tetramethylcyclopropane carboxylic acid:cyano(6-(3-fluorophenoxy)-2-pyridinyl)methyl ester.

22. The composition as defined in claim 15 wherein the compound is 2,2,3,3-tetramethylcyclopropane carboxylic acid:cyano(6-(4-fluorophenoxy)-2-pyridinyl)methyl ester.

23. A method for the kill and control of insects which comprises contacting said insects or their habitat with a composition containing an inert carrier and as the active ingredient, an insecticidally effective amount of a compound corresponding to the formula

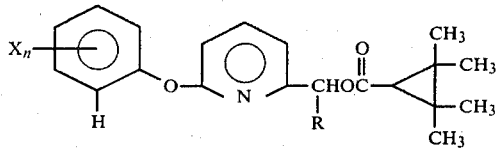

wherein n represents an integer of 0 to 2; X independently represents alkyl of 1 to 4 carbon atoms, alkoxy of 1 to 4 carbon atoms, alkylthio of 1 to 4 carbon atoms, alkylsulfinyl of 1 to 4 carbon atoms, alkylsulfonyl of 1 to 4 carbon atoms, trifluoromethyl, chloro, fluoro, bromo; n represents an integer of 0 to 2; and R represents hydrogen, cyano or ethynyl.

24. A method as defined in claim 23 wherein R is hydrogen.

25. A method as defined in claim 23 wherein R is ethynyl.

26. A method as defined in claim 23 wherein R is cyano.

27. The method as defined in claim 24 wherein the active ingredient is 2,2,3,3-tetramethylcyclopropane carboxylic acid:(6-phenoxy-2-pyridinyl)methyl ester.

28. The method as defined in claim 25 wherein the active ingredient is 2,2,3,3-tetramethylcyclopropane carboxylic acid:cyano(6-phenoxy-2-pyridinyl)-2-propynyl ester.

29. The method as defined in claim 26 wherein the active ingredient is 2,2,3,3-tetramethylcyclopropane carboxylic acid:cyano(6-phenoxy-2-pyridinyl)methyl ester.

30. The method as defined in claim 26 wherein the active ingredient is 2,2,3,3-tetramethylcyclopropane carboxylic acid:cyano(6-(4-methoxyphenoxy)-2-pyridinyl)methyl ester.

31. The method as defined in claim 26 wherein the active ingredient is 2,2,3,3-tetramethylcyclopropane carboxylic acid:cyano(6-(4-chlorophenoxy)-2-pyridinyl)methyl ester.

32. The method as defined in claim 26 wherein the active ingredient is 2,2,3,3-tetramethylcyclopropane carboxylic acid:cyano(6-(3-fluorophenoxy)-2-pyridinyl)methyl ester.

33. The method as defined in claim 26 wherein the active ingredient is 2,2,3,3-tetramethylcyclopropane carboxylic acid:cyano(6-(4-fluorophenoxy)-2-pyridinyl)methyl ester.

* * * * *